(12) United States Patent
Marx et al.

(10) Patent No.: US 7,148,190 B2
(45) Date of Patent: Dec. 12, 2006

(54) HAPTOTACTIC PEPRIDES

(75) Inventors: Gerard Marx, Jerusalem (IL); Raphael Gorodetsky, Jerusalem (IL)

(73) Assignee: Hadasit Medical Research Services & Development Company Ltd., Jerusalem (IL)

( * ) Notice: Subject to any disclaimer, the term of this patent is extended or adjusted under 35 U.S.C. 154(b) by 283 days.

(21) Appl. No.: 10/181,187

(22) PCT Filed: Jan. 21, 2001

(86) PCT No.: PCT/IL01/00057

§ 371 (c)(1),
(2), (4) Date: Oct. 8, 2002

(87) PCT Pub. No.: WO01/53324

PCT Pub. Date: Jul. 26, 2001

(65) Prior Publication Data

US 2004/0126758 A1    Jul. 1, 2004

Related U.S. Application Data

(63) Continuation-in-part of application No. 09/487,790, filed on Jan. 20, 2000, now abandoned.

(51) Int. Cl.
| | |
|---|---|
| C07K 17/00 | (2006.01) |
| C07K 17/02 | (2006.01) |
| A61K 38/10 | (2006.01) |
| A61K 35/14 | (2006.01) |

(52) U.S. Cl. .............................. 514/2; 514/8; 530/300; 530/326; 530/382; 530/345; 427/414

(58) Field of Classification Search .................... 514/2, 514/8; 530/300, 326, 382, 345; 427/414
See application file for complete search history.

(56) References Cited

U.S. PATENT DOCUMENTS

| | | | | |
|---|---|---|---|---|
| 4,455,290 A | * | 6/1984 | Olexa et al. ................ | 424/1.69 |
| 4,661,471 A | * | 4/1987 | Hawiger et al. ............. | 514/13 |
| 5,372,933 A | * | 12/1994 | Zamarron et al. ......... | 435/7.21 |
| 5,599,790 A | | 2/1997 | Altieri et al. | |
| 6,083,902 A | | 7/2000 | Cederhom-Williams | |

FOREIGN PATENT DOCUMENTS

| | | | |
|---|---|---|---|
| WO | WO 95/29686 | * | 11/1995 |
| WO | WO 99/61041 | * | 12/1999 |

OTHER PUBLICATIONS

Farrell, D. H. et al. (1994) Binding of recombinant fibrinogen mutants to platelets. J. Biol. Chem. vol. 269, pp. 226-231.*
Fornace, A. J. et al. (1984) Structure of the human gamma-fibrinogen gene. Alternate mRNA splicing near the 3' end of the gene produces gamma A and gamma B forms of gamma-fibrinogen. J. Biol. Chem. vol. 259, pp. 12826-12830.*
Moroi, M. et al. (1998) Integrin-mediated platelet adhesion. Front Biosci. vol. 3, pp. 719-728.*
Francis, C. W. et al. (1988) Carboxyl-terminal amino acid sequences of two variant forms of the gamma chain of human plasma fibrinogen. Proc. Natl. Acad. Sci. U S A. vol. 85, pp. 3358-3362.*
Attachment 1 (www.bioon.com/book/biology/genomicglossaries/proteins_glossary.asp.htm), p. 1-1.*
Redman et al. (2001) Fibrinogen biosynthesis. Assembly, intracellular degradation, and association with lipid synthesis and secretion. Ann. N. Y. Acad. Sci. vol. 936, pp. 480-495.*
Chung, D., et al., (1983), Characterization of Complementary Deoxyribonucleic Acid and Genomic Deoxyribonucleic Acid for the β Chain of Human Fibrinogen, *Biochemistry*, (22) pp. 3244-3250 (Exhibit 2).
Watala, C, et al., (1996), Microenvironmental changes in platelet membranes induced by the interaction of fibrinogen-derived peptide ligands with platelet integrins, *Eur. J. Biochem.*, (235) pp. 281-288 (Exhibit 3).
International Search Report (Exhibit 4).

* cited by examiner

*Primary Examiner*—Jon Weber
*Assistant Examiner*—Samuel Wei Liu
(74) *Attorney, Agent, or Firm*—John P. White; Cooper & Dunham LLP

(57) ABSTRACT

We disclose haptotactic peptides having sequences homologous to specific portions of the carboxy terminal sequence of fibrinogen chains. The peptides derived from fibrinogen pre-Cγ chain possess activities of cell attraction or cell attachment to a surface to which the peptide is covalently bound.

20 Claims, 3 Drawing Sheets

Haptotaxis assay with Sepharose Beads (SB) bound to the tested ligand

Haptotaxis of SB-ligand to BAEC

HF Uptake of haptotactic peptide-FITC (1hr)

Cβ preCγ

Cmfap

SEQUENCE LISTING

```
<160> NUMBER OF SEQ ID NOS: 12

<210> SEQ ID NO 1
<211> LENGTH: 20
<212> TYPE: PRT
<213> ORGANISM: Artificial sequence
<220> FEATURE:
<223> OTHER INFORMATION: Equivalent to the c-terminus of fibrogen
                        gamma-chain

<400> SEQUENCE: 1

Lys Thr Arg Trp Tyr Ser Met Lys Lys Thr Thr Met Lys Ile Ile Pro
 1               5                  10                  15

Phe Asn Arg Leu
            20

<210> SEQ ID NO 2
<211> LENGTH: 19
<212> TYPE: PRT
<213> ORGANISM: Artificial sequence
<220> FEATURE:
<223> OTHER INFORMATION: Equivalent to the c-terminus of angiopoietin-1

<400> SEQUENCE: 2

Lys Gly Pro Ser Tyr Ser Leu Arg Ser Thr Thr Met Met Ile Arg Pro
 1               5                  10                  15

Leu Asp Phe

<210> SEQ ID NO 3
<211> LENGTH: 19
<212> TYPE: PRT
<213> ORGANISM: Artificial sequence
<220> FEATURE:
<223> OTHER INFORMATION: Equivalent to the c-terminus of angiopoietin-2

<400> SEQUENCE: 3

Lys Gly Ser Gly Tyr Ser Leu Lys Ala Thr Thr Met Met Ile Arg Pro
 1               5                  10                  15

Ala Asp Phe

<210> SEQ ID NO 4
<211> LENGTH: 19
<212> TYPE: PRT
<213> ORGANISM: Artificial sequence
<220> FEATURE:
<223> OTHER INFORMATION: Equivalent to the c-terminus of Tenascin-X

<400> SEQUENCE: 4
```

Lys Gly Phe Glu Phe Ser Val Pro Phe Thr Glu Met Lys Leu Arg Pro
 1               5                  10                  15

Asn Phe Arg

<210> SEQ ID NO 5
<211> LENGTH: 17
<212> TYPE: PRT
<213> ORGANISM: Artificial sequence
<220> FEATURE:
<223> OTHER INFORMATION: Equivalent to c-terminus of Microfibril
                        associated protein

<400> SEQUENCE: 5

Lys Gly Phe Tyr Tyr Ser Leu Lys Arg Pro Glu Met Lys Ile Arg Arg
 1               5                  10                  15

Ala

<210> SEQ ID NO 6
<211> LENGTH: 8
<212> TYPE: PRT
<213> ORGANISM: Artificial sequence
<220> FEATURE:
<223> OTHER INFORMATION: Equivalent to the c-terminus of fibrinogen
                        beta-chain

<400> SEQUENCE: 6

Lys Gly Ser Trp Tyr Ser Met Arg
 1               5

<210> SEQ ID NO 7
<211> LENGTH: 10
<212> TYPE: PRT
<213> ORGANISM: Artificial sequence
<220> FEATURE:
<223> OTHER INFORMATION: Equivalent to the c-terminus of fibrinogen
                        beta-chain

<400> SEQUENCE: 7

Lys Gly Ser Trp Tyr Ser Met Arg Lys Met
 1               5                  10

<210> SEQ ID NO 8
<211> LENGTH: 10
<212> TYPE: PRT
<213> ORGANISM: Artificial sequence
<220> FEATURE:
<223> OTHER INFORMATION: Equivalent to the c-terminus of fibrinogen
                        gamma-chain

<400> SEQUENCE: 8

Lys Thr Arg Trp Tyr Ser Met Lys Lys Thr
 1               5                  10

<210> SEQ ID NO 9
<211> LENGTH: 8
<212> TYPE: PRT
<213> ORGANISM: Artificial sequence
<220> FEATURE:
<223> OTHER INFORMATION: Equivalent to the c-terminus of angiopoietin-1

<400> SEQUENCE: 9

Lys Gly Pro Ser Tyr Ser Leu Arg
 1               5

<210> SEQ ID NO 10

```
-continued

<211> LENGTH: 10
<212> TYPE: PRT
<213> ORGANISM: Artificial sequence
<220> FEATURE:
<223> OTHER INFORMATION: Equivalent to c-terminus of Microfibril
                        associated protein

<400> SEQUENCE: 10

Lys Gly Phe Tyr Tyr Ser Leu Lys Arg Pro
 1               5                  10

<210> SEQ ID NO 11
<211> LENGTH: 16
<212> TYPE: PRT
<213> ORGANISM: Artificial sequence
<220> FEATURE:
<223> OTHER INFORMATION: Haptotactic consensus sequence
<220> FEATURE:
<221> NAME/KEY: MISC_FEATURE
<222> LOCATION: (1)...(16)
<223> OTHER INFORMATION: Xaa is any amino acid or is absent

<400> SEQUENCE: 11

Lys Gly Xaa Xaa Tyr Ser Met Arg Lys Xaa Xaa Met Lys Ile Arg Pro
 1               5                  10                  15

<210> SEQ ID NO 12
<211> LENGTH: 9
<212> TYPE: PRT
<213> ORGANISM: Artificial sequence
<220> FEATURE:
<223> OTHER INFORMATION: Haptotactic consensus sequence
<220> FEATURE:
<221> NAME/KEY: MISC_FEATURE
<222> LOCATION: (1)...(9)
<223> OTHER INFORMATION: Xaa is any amino acid or is absent

<400> SEQUENCE: 12

Lys Gly Xaa Xaa Tyr Ser Met Arg Lys
 1               5
```

HAPTOTACTIC PEPRIDES

This patent application is a §371 national stage application of International Application No. PCT/IL01/00057, filed Jan. 21, 2001 which is a continuation-in-part of U.S. Ser. No. 09/487,790, filed Jan. 20, 2000 now abandoned, the contents of which are hereby incorporated into this application by reference.

FIELD OF THE INVENTION

The present invention relates to novel cell attachment peptides, designated herein as haptotactic peptides, and in particular to peptides which are homologous to specific portions of the carboxy termini of fibrinogen chains that appear in other proteins, as well as to pharmaceutical compositions comprising such haptotactic peptides and potential uses for such compositions.

BACKGROUND OF THE INVENTION

Fibrinogen is the plasma protein responsible for blood clot formation. Normal fibrinogen is a complex of 2 each of 3 chains ($\alpha,\beta$ and $\gamma$) (1–6). A variant of $\alpha$ fibrinogen (fib$_{340}$) with an extended $\alpha$ chain known as $\alpha$E fibrinogen (fib$_{420}$) that constitutes about 1% of the total fibrinogen in adult humans has more recently been discovered but its unique function is not yet clear (7–10). Thus, the four types of fibrinogen chains, $\alpha$, $\beta$, $\gamma$ and $\alpha$E, contain 610, 483, 411 and 866 amino acids, respectively (the numbering based on the Gene-bank database, accessible at ncbi.nlm.nih.gov).

Fibrinogen is not immunogenic within the same species, as attested by the use of pooled fibrin glue for clinical applications. Besides its hemostatic activity, it has been previously demonstrated that fibrin(ogen) elicits cell attachment (haptotactic) and migratory (chemotactic) responses with different cell types including mouse and human fibroblasts (MF and HF), bovine aortic endothelial (BAEC) and smooth muscle cells (SMC) (11,12).

The carboxy terminal sequences, i.e., the C-terminal 30–40 amino acids of the fibrinogen chains, are highly conserved between different species (13, 14). With the exception of the $\gamma$-chain C terminus (11,12), they have not been shown to relate to any hemostatic function of fibrinogen. A voluminous literature exists which describes the binding of fibrinogen ($\gamma$400-411) to platelets through the GPIIb/IIIa receptor and the aggregation activity of the new amino B$\beta$15-42 terminus that is exposed after release of fibrinopeptide B.

Fibrinogen fragment E was reported to exhibit angiogenic properties and to inhibit endothelial cell migration in a Boyden chamber chemotactic assay (19). The larger fragment D was reported to cause detachment of cultured endothelial cells from the extracellular matrix (ECM) substratum in a concentration and time dependent process (20).

Isolated constituent chains of fibrinogen (A$\alpha$1, A$\alpha$2 and B$\beta$) released upon activation of fibrinogen by thrombin were observed to stimulate fibroblast proliferation by 23–31% above controls, whereas isolated $\gamma$ chain had no effect (22). Human polymorphonuclear leukocytes (PMN) were shown to bind to fibrin(ogen) coated surfaces via a type 3 (CD11b/CD 18) complement receptor homologous to the GPIIb/IIIa receptor through a decamer of the $\gamma$ chain carboxy terminus (LGGAKQAGDV). Vasoactive peptides were identified corresponding to residues 43–47 of the B$\beta$ chain and 220–230 of the A$\alpha$ chain (21).

The biological activities of a few other fibrinogen breakdown products have been investigated, but the cellular activity seemed to be widely variable (23).

Functional peptide sequences previously have been disclosed on the $\gamma$-chain, including sites involved in platelet binding ($\gamma$ 400-411), leukocyte adhesion ($\gamma$ 396-411), factor XIII-crosslinking sites ($\gamma$ 398, $\gamma$ 407), a polymerization region ($\gamma$ 374-395), and fibroblast adhesion region ($\gamma$ 374-394). Thus, fibrinogen interactions with platelets and cells have been documented by a number of workers.

It has previously been disclosed by the present inventors (WO99/61041) that certain cell attachment effects of the intact fibrin(ogen) could be ascribed to small sequences at the carboxy termini of all the fibrinogen chains. Synthetic peptide fragments of the last 19–21 amino acids of carboxy termini of the $\alpha$, $\beta$ and $\gamma$ chains of normal fibrinogen and of the $\alpha$E chain (peptides termed C$\alpha$, C$\beta$, C$\gamma$ and C$\alpha$E respectively), were tested. Only C$\beta$ and C$\alpha$E sequences induced significant haptotactic responses from various cultured cell types, mostly of mesenchymal origin, such as HF, BAEC and SMC, whereas the C$\alpha$ and C$\gamma$ peptides did not exhibit significant haptotactic (cell attachment) activity. The active peptide C$\beta$ was shown to be rapidly taken up by the cells in a non-saturatable manner. None of the disclosed peptides affected the rate of cell proliferation.

The identification of new haptotactic epitopes would have a number of applications, enabling more specific intervention in the wound healing process and the development of novel therapeutic compositions or devices. Furthermore, novel diagnostic tests to monitor cellular haptotactic responses could potentially be developed. Such peptides may have the ability to elicit haptotactic responses from cells, with no need to utilize the whole fibrinogen molecule and its attendant safety and regulatory issues.

Thus, there is a recognized need for, and it would be highly advantageous, to have peptides with specifically determined cellular effects, such as chemotactic or haptotactic properties, which do not require the presence of the entirety of the fibrin(ogen), or the entirety of other proteins containing a homologous sequence.

SUMMARY OF THE INVENTION

It is an object of the present invention to identify and characterize haptotactic peptides with novel amino acid sequences that are homologous to known haptotactic peptides present within the carboxy termini of fibrinogen chains.

Haptotactic peptides are characterized in that they induce cell attachment to a surface to which such a peptide is covalently bound, inasmuch as the number of cells attached to such a surface will be at least 50% greater than the number of cells attached to the same surface absent the peptide. Preferably, the number of cells attached to such a surface will be at least 70% greater than the number of cells attached to the same surface absent the peptide. More preferably, the number of cells attached to such a surface will be at least double the number of cells attached to the same surface absent the peptide.

It is a first object to identify additional haptotactic peptides within or adjacent to the carboxy termini of fibrinogen chains. It is a further object of this invention to identify and characterize novel haptotactic peptides from additional proteins or polypeptides, containing at least one amino acid sequence homologous to such a fibrinopeptide. These novel haptotactic peptides are characterized in that they induce cell attachment to a surface to which such a peptide is covalently bound, inasmuch as the number of cells attached to such a surface will be at least 50% greater preferably 70% greater and more preferably double the number of cells attached to the same surface absent the peptide.

The degree of homology of the novel peptides to the fibrinopeptides will be at least 50%, preferably 60%, more preferably 70% and most preferably 80% or greater.

It is another object of the present invention to provide pharmaceutical compositions comprising as an active ingredient a novel haptotactic peptide according to the invention. It is another object of the present invention to provide medical implants or devices comprising as an active ingredient a novel haptotactic peptide according to the invention.

It is yet another object of the present invention to provide methods of using haptotactic peptides according to the invention in the treatment of a wound, disease or disorder comprising administering to an individual in need thereof a therapeutically effective amount of a haptotactic peptide according to the invention.

It is yet another object of the present invention to provide methods of using haptotactic peptides according to the invention in the treatment of a wound, disease or disorder comprising implanting into an individual in need thereof a medical implant or device comprising as an active ingredient a novel haptotactic peptide according to the invention.

It is another object of the present invention to provide pharmaceutical compositions comprising mixtures or combinations of haptotactic peptides according to the present invention. In this aspect the term combination may include both covalent attachments or non-covalent complexes or non-covalent mixtures. It is yet another object of the present invention to provide pharmaceutical compositions comprising at least one haptotactic peptide, further comprising at least one additional drug or biologically active agent. The additional drug or biological agent may be present in the composition as a non-covalent mixture or as a covalent conjugate with the haptotactic peptide.

It is still another object of the present invention to provide such haptotactic peptides useful for cell culture and cell separation. It is yet another object of the present invention to provide such haptotactic peptides useful for fabricating novel cell-containing structures, including biomedical devices. It is yet another object of the present invention to provide such haptotactic peptides useful for coating natural or synthetic matrices. It is a further object of the present invention to provide such haptotactic peptides useful for accelerating the migration and attachment of cells to implants. It is yet another object of the present invention to provide a haptotactic peptide for attracting selected cell types into a biomedical device. It is yet another object of the present invention to provide such haptotactic peptides useful for targeting drug and biological factor uptake into different cell types.

These and other objects of the present invention are explained in greater detail in the description, Figures and claims below.

The novel peptide sequences of the present invention are homologous to certain known peptides of fibrin(ogen). They are derived either from hitherto undisclosed active fragments of fibrinogen or from certain other proteins or polypeptides containing homologous sequences, that retain certain desired properties of the entire molecule, such as cell adhesive effects, as defined above.

Within the scope of the present invention it is to be understood that the haptotactic peptides disclosed are preferred embodiments and intended to be construed as encompassing shorter active fragments thereof as well as homologs, derivatives and analogs, as defined hereinbelow.

Certain currently more preferred embodiments according to the invention include the following 19–21 mer peptides:

KTRWYSMKKTTMKIIPFNRL (peptide preCγ, SEQ ID NO: 1;)
KGPSYSLRSTTMMIRPLDF (peptide-C-ang1, SEQ ID NO:2;)
KGSGYSLKATTMMIRPADF (peptide-C-ang2, SEQ ID NO:3);
KGFEFSVPFTEMKLRPNFR (peptide-C-tenX, SEQ ID NO:4), and
KGFYYSLKRPEMKIRRA (peptide-C-mfap, SEQ ID NO:5), Additional currently preferred embodiments include shorter sequences that were also determined to be haptotactic. The currently preferred specific sequences comprising 8–10 mer cell attachment peptides are:

KGSWVSMR (peptide-C$\beta_8$, SEQ ID NO:6); or
KGSWYSMRKM (peptide-C$\beta_{10}$, SEQ ID NO:7)
KTRWYSMKKT (peptide-PreC$\gamma_{10}$, SEQ ID NO:8);
KGPSYSLR (peptide-C-ang1$_8$, (SEQ ID NO:9) and
KGFYYSLKP (peptide-C-mfap$_{10}$, (SEQ ID NO: 10).

The 19–21 mer sequences as set forth in SEQ IDs # 1, 2, 3, 4 and 5 are equivalent to the C terminal amino acids of preCγ, C-ang1, C-ang2, C-tenX, and C-mfap, respectively.

The 8–10-mer sequences as set forth in SEQ IDs # 6, 7, 8, 9 and 10 are homologous to the first 8–10 amino acids sequences of the 19–21 mer haptotactic Cβ and pre-Cγ, C-mfap and C-ang1, respectively.

Based on the high attachment activity of the synthetic 19–21 mer peptides homologous to sequences in fibrinogen Cβ and preCγ chains as well as the other proteins with homologous sequences, a haptotactic consensus sequence called HAPT$_{15}$ (SEQ ID NO:11) has been constructed comprising the amino acids:

KGX$_a$X$_b$YSMRKX$_c$X$_d$MKIRP;

wherein X denotes an amino acid, or may be absent thereby forming a direct bond. Extensions at the N or C termini of this sequence are explicitly encompassed within the scope of the present invention. It should be noted that conservative replacements of the amino acid residues of this consensus sequence are also encompassed within the scope of the present invention, as is well known in the art.

Based on the activity of the synthetic 8–10 mer sequences a shorter haptotactic consensus sequence HAPT$_9$ epitope (SEQ ID NO:12) was constructed:

KGX$_a$X$_b$YSMRK wherein X denotes an amino acid or may be absent thereby forming a direct bond.

The HAPT$_{15}$ and HAPT$_9$ consensus sequences themselves, as well as analogs or derivatives comprising an additional spacer moiety or rearrangement for proper geometrical configuration, are also disclosed herein as haptotactic peptides of the present invention. It is intended to be understood that all known peptides encompassed within the generic formulae are explicitly excluded, including but not limited to the known haptotactic peptides of Cβ and CαE.

BRIEF DESCRIPTION OF THE DRAWINGS

The invention is herein described by way of example only, with reference to the accompanying drawings, wherein.

DETAILED DESCRIPTION OF THE INVENTION

Figure 1:
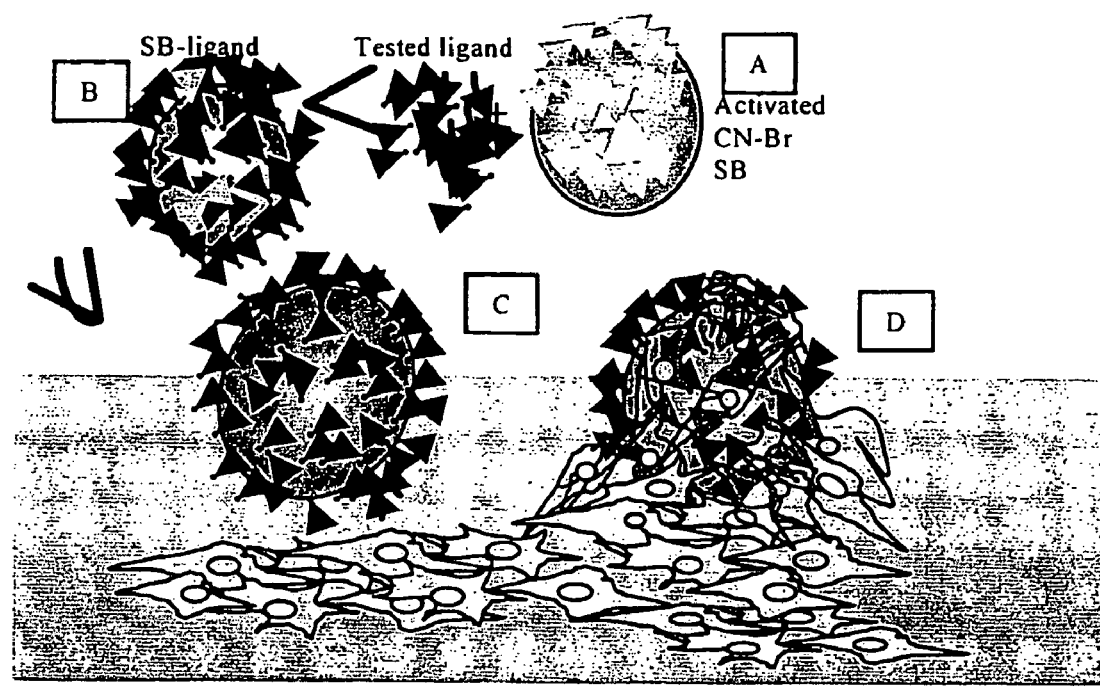
FIG. 1. Schematically depicts the principle underlying the haptotaxis assay utilizing peptide-coated Sepharose beads (SB). The CNBr activated SB (A) are reacted with the peptide to be tested resulting in SB-ligand (B). These are dropped onto a near confluent cell culture (C) and incubated. After a few hours the cells begin to attach the SB coated with haptotactic ligand (D). The fraction of SB-peptide attached to the cell layer represents % haptotaxis. Non-coated SB or SB coated with non-reactive ligands (i.e. SB-albumin) do not attach.

The present invention relates to novel peptides, which are homologous to haptotactic epitopes of fibrinogen, as well as to uses for these sequences in vivo as well as in vitro. For example, these peptide sequences have potential medical uses, including but not limited to therapeutic and diagnostic uses. The synthetic peptide sequences are homologous to regions of the fibrin(ogen) molecule, yet retain certain desired properties of the entire molecule, such as cell adhesive effects.

In particular, these cell attachment peptides comprise novel sequences homologous to 19–21 amino acids sequence of the carboxy termini of the β chain and αE chains of fibrinogen, which are now disclosed in other regions of fibrinogen as well as in other proteins.

The term "fibrin(ogen)" is known in the art and denotes either fibrinogen or fibrin or a mixture of fibrin and fibrinogen, and is referred to herein according to this definition. Hereinafter, the term "biologically active" refers to molecules, or complexes thereof, which are capable of eliciting an effect in a biological system. Hereinafter, the term "fragment" refers to a portion of a molecule or a complex thereof, in which the portion includes substantially less than the entirety of the molecule or the complex thereof.

The term "amino acid" refers to compounds which have an amino terminus and carboxy terminus, preferably in a 1,2- 1,3-, or 1,4- substitution pattern on a carbon backbone. α-Amino acids are most preferred, and include the 20 natural amino acids (which are L-amino acids except for glycine), which are found in proteins, the corresponding D-amino acids, the biosynthetically available amino acids which are not found in proteins (e.g., 4-hydroxy-proline, 5-hydroxy-lysine, citrulline, ornithine, canavanine, djenkolic acid, β-cyanolanine), and synthetically derived α-amino acids, such as amino-isobutyric acid, norleucine, norvaline, homocysteine and homoserine. β-Alanine and γ-amino butyric acid are examples of 1,3 and 1,4-amino acids, and many others are well known to the art. Statine-like isosteres (a dipeptide comprising two amino acids wherein the CONH linkage is replaced by a CHOH), hydroxyethylene isosteres (a dipeptide comprising two amino acids wherein the CONH linkage is replaced by a CHOHCH$_2$), reduced amide isosteres (a dipeptide comprising two amino acids wherein the CONH linkage is replaced by a CH$_2$NH linkage) and thioamide isosteres (a dipeptide comprising two amino acids wherein the CONH linkage is replaced by a CSNH linkage) are also useful residues for this invention.

As used herein "peptide" indicates a sequence of amino acids linked by peptide bonds. The peptide analogs of this invention comprise a sequence of amino acids of 7 to 24 amino acid residues, preferably 8 to 21 residues, each residue being characterized by having an amino and a carboxy terminus.

Hereinafter, the term "peptide" refers a sequence of amino acids, while the term "peptidomimetic" refers to analogues and mimetics having substantially similar or identical functionality to that of the haptotactic peptide which it is intended to mimic, including analogues having synthetic and natural sequences.

Hereinafter, the term "haptotactic peptide" refers to amino-acid sequences or analogues or derivatives or peptido-mimetics thereof, which are capable of eliciting attachment responses from cells, whereby the attachment of the cells in the presence of the haptotactic molecule is at least 50% greater than that in the absence thereof.

Hereinafter the term "epitope" refers to the active site on a complex molecule, which can react with antibodies or cell receptors. The term "epitope" is used herein, but is not limited to describing relatively short linear peptidic sequences on polypeptides or proteins (such as 8–10 amino acids in length) which can induce cell haptotaxis by interacting with cell attachment sites. Epitopes may also be formed by amino acid residues at sites which are not contiguous in the primary sequence of the polypeptide.

Hereinafter, the term "wound-healing cells" refers to those cells, which promote healing of a wound, including, but not limited to, fibroblasts, smooth muscle endothelial cells, osteoblasts and chondrocytes.

Based on the known (WO99/61041) activity of the CαE and its sequence homology to Cβ, it is now disclosed that we have identified and characterized novel haptotactic peptides. One novel haptotactic peptide, which is homologous to the Cβ 20-mer sequence, comprises the fragment adjacent to, i.e. just preceding, the C-terminal of the γ chain, termed herein preCγ (γ 366-386). We have further identified other proteins that contain regions with significant homology to Cβ. Table 1 summarizes these proteins in sub-sets based on their biological function (Table 1; 1st column) including hemostasis (fibrinogen), modulators of angiogenesis (angiopoietins) (24–30), microfibril associated glyco-protein of the vasculature (microfibril associated protein 4) (31–34) and extracellular proteins of the tenascin family (35–37).

For example, angiopoietin 1 (ang1) and angiopoietin 2 (ang2) (MW~130 kDa) (25–28) contain the haptotactic motif shared by fibrinogen Cβ and preCγ (the degree of homology having a statistical significance of $p<0.001$). These factors are secreted by cells to modulate vasculature formation in normal and cancer tissue. While ang1 serves as a stimulator of capillary development, ang2 is an inhibitor thereof. The receptors for these angiopoietins have been identified as the tyrosine kinase receptors Tie 1- and Tie-2 (26–30).

The family of tenascins, which contains a fibrinogen-like domain (34–37) also contain a sequence homologous to Cβ. Tenascins have been associated with the growth of neurons, but are ubiquitous and may serve other developmental functions, including binding to and modulating membrane sodium channels. Cell receptors identified to date for tenascins include integrins $\alpha_8\beta_1$ and $\alpha_9\beta_1$. Some tenascins are organized as hexamers.

Smith-Magenis syndrome (SMS) is a clinically recognizable multiple congenital anomaly/mental retardation syndrome associated with deletion of chromosome 17p11.2. The gene encoding a human microfibril-associated glycoprotein-4 (MFAP4) has been mapped to the SMS region that has a fibrinogen-like domain. A full-length cDNA corresponding to the MFAP4 gene contains a coding region of 255 amino acids. Deletion of the MFAP4 gene locus in SMS patients has been considered in the pathogenesis of this genetic disorder (34–37).

TABLE 1

Extended family of proteins containing a sequence homologous to the Cβ

| Biol. Function | Protein Name | Code name | 1 2 3 4 5 6 7 8 9 10 11 12 13 14 15 16 17 18 19 20<br>17–21 mer peptide (synthesized) | Position | P value |
|---|---|---|---|---|---|
| Fibrinogen | β chain | Cβ | K G S W S M K K T T M K I I P F N R L T | 463-83 | 0 |
| Clotting | αE chain | CαE | R G A D Y S L R A R M K P L V T Q | 847-66 | 0.000001 |
| | internal γ chain | preCγ | K T R W I M K K T T M K I I P F N R L T | 366-86/411 | 0.0001 |
| Vasculo-genesis | Angiopoietin-1 | Cang1 | K G P S Y S L R S T T M K I P L D F | 480-98 | 0.046 |
| | Angiopoietin-2 | Cang2 | K G S G Y S L K A T T M H P A D F | 478-96 | 0.0007 |
| | Microfibril assoc. GP4 | Cmfap | K G F Y F L K R P E M K R A | 239-55 | 0.0006 |
| Develop. | Tenascin-r (restrictin) | CtenR | K G H E H P F W E M R M R N H R L | 1320-40/1358 | 0.01 |
| | Tenascin-x | CtenX | K G F E V P F T E M L R R N F R S | 641-61/673 | 0.03 |
| | Tenascin-c | CtenC | K G H E H Q F A E M K L R S N F R N | 2166-86/2201 | 0.01 |

Full homology: Dark gray
Positive Homology: light gray

Homology is defined as meaning positional identity relative to the sequence of interest, as employed by the genebank data bases. Partial sequence identity (termed "positive homology") also adds to the score by defining certain amino acids as equivalent to one another (i.e. positive homology groupings are: S=T=N; R=K=Q; F=Y; V=M=L=I).

The novel haptotactic peptides (comprising homologous sequence variants of known haptotactic peptides) were synthesized as individual peptides, namely: Fibrinogen γ chain peptide, designated herein as preCγ, (SEQ ID NO:1); Angiopoietin 1 peptide, designated herein as C-ang1, (SEQ ID NO:2); angiopoietin 2 peptide, designated herein as C-ang2 (SEQ ID NO:3); tenascin X peptide designated herein as C-tenX (SEQ ID NO:4), and microfibril associated glycoprotein 4 peptide designated herein Cmfap (SEQ ID NO:5).

Active fragments of these cell attachment peptides are also now disclosed comprising 8–10 amino-acid long peptides (8–10 mers) of the above described haptotactic peptides such as:

Cβ$_8$, (SEQ ID NO:6); Cβ$_{10}$ (SEQ ID NO:7);
PreCγ$_{10}$, (SEQ ID NO:8);
C-ang1$_{10}$, (SEQ ID NO:9) and
C-mfap$_8$, (SEQ ID NO: 10).

The sequences of these peptides are given in Tables 2 and 3 below.

TABLE 2

Name, composition and codes of haptotactic 19–21 mer peptides

| Name | 1 | 2 | 3 | 4 | 5 | 6 | 7 | 8 | 9 | 10 | 11 | 12 | 13 | 14 | 15 | 16 | 17 | 18 | 19 | 20 | 21 | Code |
|---|---|---|---|---|---|---|---|---|---|---|---|---|---|---|---|---|---|---|---|---|---|---|
| C β | NH$_2$ K | G | S | W | Y | S | M | R | K | M | S | M | K | I | R | P | F | F | P | COOH Q | Q | known peptide (SEQ ID NO:14) |
| C αE | R | G | A | D | Y | S | L | R | A | V | R | M | K | I | R | P | L | V | T | Q | | known peptide (SEQ ID NO:15) |
| PreC γ | K | T | R | W | Y | S | M | K | K | T | T | M | K | I | I | P | F | N | R | L | | SEQ ID NO:1 |
| C ang1 | K | G | P | S | Y | S | L | R | S | T | T | M | M | I | R | P | L | D | F | | | SEQ ID NO:2 |
| C ang2 | K | G | S | G | Y | S | L | K | A | T | T | M | M | I | R | P | A | D | F | | | SEQ ID NO:3 |
| C tenX | K | G | F | E | F | S | V | P | F | T | E | M | K | L | R | P | R | N | F | R | | SEQ ID NO:4 |
| C mfap | K | G | F | Y | Y | S | L | K | R | P | E | M | K | I | R | R | A | | | | | SEQ ID NO:5 |

Table 3 shows the names, codes and sequences of 8–10 mer peptides, which were synthesized, and which were haptotactic when tested with cultured cells.

TABLE 3

Name, composition and codes of haptotactic 8–10 mer peptides

| Name | 1 | 2 | 3 | 4 | 5 | 6 | 7 | 8 | 9 | Code |
|---|---|---|---|---|---|---|---|---|---|---|
| Cβ 8 mer | K | G | S | W | Y | S | M | R | | SEQ ID NO:6 |
| Cβ 10 mer | K | G | S | W | Y | S | M | R | K M | SEQ ID NO:7 |

TABLE 3-continued

Name, composition and codes of haptotactic 8–10 mer peptides

| Name | 1 | 2 | 3 | 4 | 5 | 6 | 7 | 8 | 9 | Code |
|---|---|---|---|---|---|---|---|---|---|---|
| Pre Cγ 10 mer | K | T | R | W | Y | S | M | K | K T | SEQ ID NO:8 |
| Cang-1 10 mer | K | G | P | S | Y | S | L | R | S T | SEQ ID NO:9 |
| C mfap 8 mer | K | G | F | Y | Y | S | L | K | | SEQ ID NO 10 |

Hereinafter, the term "haptotactic peptide" refers to peptides shown in Tables 1, 2 and 3, as well as to analogues, derivatives, or peptido-mimetics thereof, which are capable of eliciting attachment responses from cells.

Based on the high attachment activity of the synthetic 19–21 mer peptides homologous to sequences in fibrinogen Cβ and preCγ chains as well as the other proteins with homologous sequences, a haptotactic consensus sequence called HAPT$_{15}$ (SEQ ID NO:11) has been constructed comprising the amino acids:

KGX$_a$X$_b$YSMRKX$_c$X$_d$MKIRP;

wherein X denotes an amino acid, or may be absent thereby forming a direct bond. Extensions at the N or C termini of this sequence are explicitly encompassed within the scope of the present invention. It should be noted that conservative replacements of the amino acid residues of this consensus sequence are also encompassed within the scope of the present invention, as is well known in the art.

Based on the activity of the synthetic 8–10 mer sequences a shorter haptotactic consensus sequence HAPT$_9$ epitope (SEQ ID NO:12) was constructed:

KGX$_a$X$_b$YSMRK

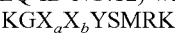

wherein X denotes an amino acid or may be absent thereby forming a direct bond.

The haptotactic peptides of the present invention are contemplated for many different uses, including but not limited to the treatment of a wound bed. Additional uses of the haptotactic peptides of the present invention include, but are not limited to, the separation of different types of cells from mixed cell cultures, the implantation of peptide-coated prosthetic devices, the identification and analysis of cell receptor mechanisms, the design of peptide-derivatized drugs to augment drug delivery and for diagnostic purposes. Furthermore, as explained in greater detail below, the haptotactic peptides of the present invention or their DNA or RNA sequences can also be used as tools for biological analysis and for further research and development.

These contemplated compositions, composites and uses of the haptotactic peptides of the present invention are outlined in the examples below and are intended as illustrations only and are not meant to be limiting in any way.

EXAMPLES

The present invention is drawn towards novel cell attachment epitopes and in particular to novel peptides which are homologous to regions of the carboxy termini of fibrinogen chains. Methods of using these peptidic sequences are also contemplated, including methods for the promotion of wound healing, for use as pharmaceutical compositions either per se or in conjunction with a medical device or implant, for the separation of cells from mixed populations, for the identification and analysis of cell receptor mechanisms, for use in augmenting drug delivery, prevention of restenosis and for diagnostic purposes.

The principles and operation of the invention, using peptidic amino acid sequences of fibrin and homologous sequences according to the present invention may be better understood with reference to the following non-limiting illustrative examples.

The peptides of the present invention were synthesized and tested in cell culture systems as described below in the section entitled "Experimental Procedure". The results are given in the section entitled "Results".

Essentially, specific peptides in Tables 2 and 3 were synthesized and covalently attached to Sepharose beads, to form SB-peptide (e.g., SB-preCγ, SB-C-ang1, or SB C-tenX). Fibrinogen was similarly covalently attached to Sepharose beads, to form SB-Fib. The SB-ligand combination was then incubated with cultured cells. The data as shown in the "Results" section, indicated that a family of peptides homologous to the fibrinogen β-chain carboxy termini appeared to be potent for cell binding, showing potency equivalent to that of the parent fibrinogen molecule.

The binding experiments with FITC-tagged peptides also indicated that the haptotactic peptides could self aggregate as well as bind to fibrinogen, fibrin and liposomes. From a biophysical perspective, these results strongly suggest that the hydrophobic C-termini of the β-chain and analogues found in the αE chain and the internal γ-chain, probably play a role in fibrin self-assembly during the various polymerization interactions it undergoes following thrombin activation.

The peptides of the above invention are significantly homologous to one another. From the perspective of fibrinogen biology, these sequences are highly conserved. Based on the lack of immunogenicity of fibrinogen itself, these haptotactic fibrino-peptides are probably non-immunogenic, and advantageously are therefore not expected to elicit immune responses. Structure/Function studies were performed to identify smaller active regions of the haptotactic peptides homologues to the fibrinogen Cβ. Selected modifications of the 19–21 mer peptides covalently bound to Sepharose beads were carried out and their haptotactic activity evaluated.

The tools and techniques arising from these haptotactic peptides will find application in diverse fields associated with cell manipulation, wound healing, targeted drug delivery and tissue engineering.

Experimental Procedures

Preparation of Peptides

Synthesis of custom made C-terminal peptides: The peptides sequences presented in Tables 2 and 3 were synthesized using standard procedures, by commercial laboratories (Novatide Ltd., Haifa, Israel; SynPep Labs, California, US; New York Blood Center Microchemistry Lab, New York, US). The experiments employed peptides that were >85–95% pure as determined by HPLC/mass-spectrometry.

Covalent coupling of peptides or proteins to Sepharose beads: Peptides, fibrinogen and other proteins were covalently bound to CNBr-activated Sepharose 4B beads (Pharmacia, Piscataway, N.J.) in a procedure previously used to bind fibrinogen, thrombin and BSA (15,16). Concentrations of peptides bound to SB in different preparations were in the range of 2–7 μM. SB coated with either BSA, fibrinogen, fibronectin or thrombin were similarly prepared. The coated SB were stored in saline at 4° C. with 0.1% azide. Before testing with cell cultures, the beads were washed 3–5 times in sterile saline to remove all traces of azide.

SB Haptotaxis assay: The attachment of SB-ligand to cells in nearly confluent cultures was measured as previously described (15,16). Essentially, about 20–150 μl of suspended (50% v/v) SB-peptide or SB-protein were added to 6–24 well plates with near confluent cell cultures and dispersed by gentle shaking for 1 min. The plates were then incubated for up to 4 days. At different time points, the number of SB tethered to cells was counted with an inverted phase microscope. Typically, approximately 300 SB (but not less then 200) were counted in each well, and the ratio of the number of SB attached to the cells in each well, was calculated relative to the total number of SB. Only SB coated with haptotactic materials became attached to the cell layer, ultimately to be engulfed by cells and tethered to the plate. Without a ligand or coated with a neutral molecule such as BSA (control), none of the SB became attached to cells on the plate.

Percent SB attached to the cell surface at different time intervals provided a quantitative assay of the degree and the kinetics of the haptotactic response. At least 3 wells were measured for each variant and each experiment was repeated at least 3 times.

Monitoring cell number with the MTS assay: The MTS calorimetric assay (CellTitre 96 Aqueous Assay by Promega) was used to assay cell proliferation with peptide levels ranging up to 100 μg/ml and to evaluate the number of viable cells obtained in the adhesion assays. The MTS assay is based on dehydrogenate conversion of MTS by viable cells to colored tetrazolium salt and performed in 96 well plates, as previously described (15,16). The optical density (OD) of the dye was measured at 492 nm by a computerized microplate reader (Anthos HT-II, Salzburg). The OD of the dye was calibrated to correlate linearly with the cell number. The plating density and incubation conditions were optimized for each cell type.

Fluorescence microscopy and confocal laser fluorescence microscopy: Light and fluorescent microscopy were carried out using an Olympus system. Confocal laser microscopy was done with a computerized Zeiss Confocal Axiomate microscope (LSM410) with multiple excitation wavelengths. For examination of cell interaction with FITC-peptides, the cells were grown on glass coverslips to near confluence, then incubated with 10 μg/ml FITC-tagged peptides at room temperature. At different time points, the cells were washed and fixed in 0.5% buffered glutaraldehyde. Coverslips with the cells were placed on a microscope slide with PBS-glycerol 80% with 2% DABCO and examined. The representative fields of cells were visualized by phase contrast Numarski optics. Fluorescence intensity at the FITC wavelength (excitation 488 nm, emission 515 nm) and scans were stored in the computer for further image reconstruction Peptide Binding to Fibrin(ogen):

FITC-tagged peptides (10 μg/ml) were mixed with either SB-Fib, SB-peptide incubated for 1 hour at ambient temperature, and visualized by confocal fluorescent microscopy. Alternately, 100 μl of fibrin clot (2.4 mg/mL) was formed from fibrinogen and thrombin. After clot formation, 100 μl FITC-tagged peptides (10 μg/ml) were layered onto the clot, incubated for 1 hour at ambient temperature. The clot was washed with Tris buffer and visualized by confocal fluorescent microscopy.

Structure/Function Tests

Some structure function tests were carried out by measuring the haptotactic response of a given cell to SB-peptide before and after treating the SB-ligand with either trypsin, or oxidation conditions or after undergoing acetylating reaction to acetylate free amines. Based on the results with such treatments with 19–21 mer peptides, smaller 8–10 mer peptides were synthesized, coupled to SB and tested for haptotactic activity, according to the methods described above.

Monitoring Peptide Uptake by Cells by Fluorescence Microscopy

The cells examined were grown in 6-well plates on cover slips to reach near confluence. At the time of examination, the cover slips were inverted and put on a microscope slide supported by 2 thin spacers so that a thin gap (~2 mm) was left between the cells on the coverslip and the slide. This was filled with culture medium. To follow the uptake, 10 μg/mL FITC-labeled peptide was added into the culture medium in the gap. At different time points, medium was replaced with fresh medium and the fluorescence was viewed and photographed, using an Olympus fluorescent microscope system.

Coupling Haptotactic Peptide to Cellulose Sponge and Testing for Cellularization:

Dissolve peptide in minimum dimethyl sulfoxide DMSO, make <0.1 mM in phosphate buffer. Mix 1 mL of DSS (disuccinimidyl subarate) in DMSO (2.5 mM) in phosphate buffer and incubate with sponge for 30 min. at room temperature. Stop reaction by adding 1 mL Tris-saline buffer.

Pieces of peptide-coated sponge or untreated control were mixed with trypsinized fibroblasts (HF) or other cell types in cell culture medium and incubated. After 3–21 days incubation, sponge samples were removed, fixed with 95% alcohol and 0.1 mM propidium iodide (PI) was added to stain the cell nuclei. The sample was rinsed and examined by confocal fluorescent microscopy.

Results

Example 1

Summary of Haptotactic Effect of 19–21 mer Peptides with Fibroblasts (HF), Endothelial Cells (BAEC) and Smooth Muscle Cells (SMC).

The % Haptotaxis was obtained by monitoring the attachment of 19–21 mer peptide-coated Sepharose beads (SB-peptide) onto a near confluent cell layer. Periodically (i.e. 24 hr), the fraction of SB-peptide bound to the cell layer was counted out of a field of 200 or 300 SB total. The results demonstrate that the peptides SEQ ID 1–5 are haptotactic as they can render an otherwise neutral SB attractive to cells at levels equivalent to fibrinogen.

TABLE 5

Haptotactic 19–21 mers

| Source Protein | Code | SB-ligand | Pep. Code | % Haptotaxis 24 hr | | |
|---|---|---|---|---|---|---|
| | | | | EC | HF | SMC |
| SB only (control) | | None | | 0 | 0 | 0 |
| Fibrinogen (control) | | Fib | | 100 | 97 | 99 |
| Fib α chain (control) | 7 | Cα | None | 0 | 0 | 0 |
| Fib β chain | 9 | Cβ | known peptide (SEQ ID NO:14) | 94 | 98 | 93 |
| Fib αE chain | 71 | CαE | known peptide (SEQ ID NO:15) | 77 | 77 | 4 |
| Fib γ chain | 70A | preCγ | SEQ ID NO:1 | 99 | 98 | 95 |
| Fib γ chain | 70 | Cγ | None | 30 | 0 | 0 |
| Angiopoietin-1 | | C-ang1 | SEQ ID NO:2 | 81 | 63 | 67 |
| Angiopoietin-2 | | C-ang2 | SEQ ID NO:3 | 77 | 91 | 96 |
| Tenascin X | | C-tenX | SEQ ID NO:4 | 41 | 94 | 100 |
| Microfibril assoc. protein | | C-mfpa | SEQ ID NO:5 | 76 | 95 | 100 |

Example 2

Structure/Function Tests of 19–21 mer Peptides

In order to identify smaller active regions of the haptotactic peptides homologues to the fibrinogen Cβ, selected modifications of the 19–21 mer peptides covalently bound to sepharose beads were carried out and their residual haptotactic activity evaluated. Thus, it was noted that trypsin significantly reduced haptotactic activity of the Cβ but not the C-ang1. Acetylation of K and R moieties in Cβ reduced % haptotactic response of SMC and HF, but did not affect the responsiveness of EC. Oxidation of the M group particularly reduced the attractiveness of the peptides for HF. As only Cβ has an internal lysine (K) site capable of being digested by trypsin, and considering the lack of activity of the shorter Cβ12–21 (not shown here), this indicates that the first 8–10 amino acids might be adequate for a minimal haptotactic epitope.

TABLE 6

Structure/function tests of SB-peptide with cells

| SB-Ligand | Treat | % Haptotaxis EC | SMC | HF | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|---|---|---|
| SB-Cβ (SEQ ID NO:14) | none | 100 | 91 | 90 | K | G | S | W | Y | S | M | R | K | M | S | M | K | I | R | P | F | F | P | Q | Q |
|  | trypsin | 0 | 0 | 10 |  |  |  |  |  |  |  |  | • |  |  |  |  |  |  |  |  |  |  |  |  |
|  | acetyl | 100 | 60 | 12 |  |  |  |  |  |  |  | • | • |  |  |  | • |  | • |  |  |  |  |  |  |
|  | oxidize | 100 | 80 | 40 |  |  |  |  |  |  | • |  |  | • |  | • |  |  |  |  |  |  |  |  |  |
| SB-C-ang1 (SEQ ID NO:2) | none | 100 | 50 | 3 | K | G | P | S | Y | S | L | R | S | T | T | M | M | I | R | P | L | D | F |  |  |
|  | trypsin | 90 | 40 | 0 |  |  |  |  |  |  |  | • |  |  |  |  |  |  |  |  |  |  |  |  |  |
|  | acetyl | 100 | 95 | 0 |  |  |  |  |  |  |  | • |  |  |  |  |  |  |  |  |  |  |  |  |  |
|  | oxidize | 100 | 92 | 3 |  |  |  |  |  |  |  |  |  |  |  | • | • |  |  |  |  |  |  |  |  |
| SB-preCγ (SEQ ID NO:1) | none | 100 | 100 | 60 | K | T | R | W | Y | S | M | K | K | T | T | M | K | I | I | P | F | N | R |  |  |
|  | trypsin | 0 | 0 | 0 |  |  |  |  |  |  |  | • | • |  |  |  | • |  |  |  |  |  |  |  |  |
|  | acetyl | 100 | 100 | 90 | • |  |  |  |  |  |  | • | • |  |  |  | • |  |  |  |  |  |  |  |  |
|  | oxidize | 100 | 93 | 3 |  |  |  |  |  |  | • |  |  |  |  | • |  |  |  |  |  |  |  |  |  |

• denotes amino acid modified by treatment

These data suggested that the lysine (K) at position 9 was important for the haptotactic activity of Cβ, and further suggested that the sequences 1–10 might be critical to the haptotactic activity of the peptides. Based on these results (summarized in Table 6, a number of 10-mer peptides were synthesized and tested for haptotactic activity (see Table 7).

Example 3

Summary of Haptotactic Effects of 8–10-mer Peptides with Fibroblasts (HF), Endothelial Cells (BAEC) and Smooth Muscle Cells (SMC).

Figure 2A:
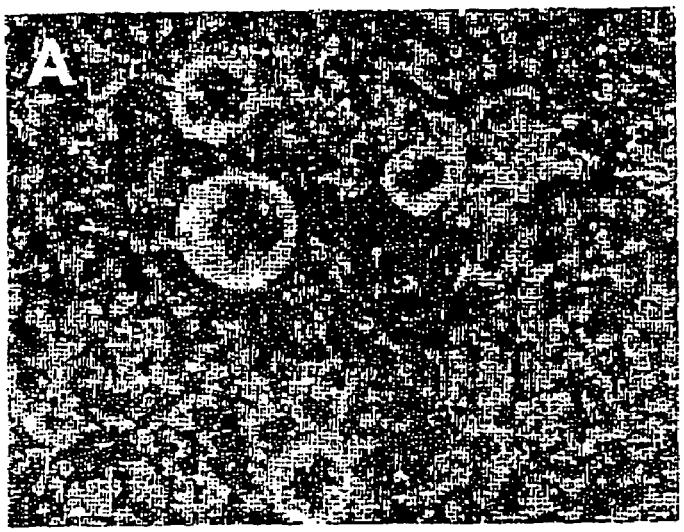
FIG. 2. Micrographs of SB-ligand reacting with endothelial cells (BAEC) after 2 days incubation. A: SB control, B: SB coated with preCγ, (SEQ ID NO:1) C: SB coated with Cang1 (sequence ID#2). By contrast to underivatized SB that do not attract cells, SB coated with reactive ligands become attached to the cell monolayer.
Figure 2B:
Figure 2C:

% Haptotaxis was monitored by following up the attachment of 10-mer peptide-coated Sepharose beads (SB-peptide) onto a near confluent cell layer (FIGS. 1 and 2). Periodically, the fraction of SB-peptide bound to the cell layer was counted out of a field of 200 or 300 SB total.

TABLE 7

Haptotactic 8–10 mers

| Source Protein | SB-ligand | Peptide Code | % Haptotaxis 24 hrs EC | HF | SMC |
|---|---|---|---|---|---|
| None (control) | None (control) |  | 0 | 0 | 0 |
| Fib β chain | RG-1 Cβ 8 mer | SEQ ID NO:6 | 88 | 79 | 93 |
| Fib γ chain | Pre Cγ 10 mer | SEQ ID NO:8 | 100 | 100 | 100 |
| Angiopoietin-1 | RG-2 C-ang1 8 mer | SEQ ID NO:9 | 75 | 45 | 4 |
| Microfib. ass. prot. | C mfap 10 mer | SEQ ID NO:10 | 100 | 99 | 100 |
| Tenascin | Ten X 10 mer | SEQ ID NO:13 | 1 | 0 | 0 |

The results demonstrate that the 8–10 mer peptides of SEQ ID 6–10 are indeed haptotactic as they can render an otherwise neutral SB attractive to cells.

Example 4

Effect of Haptotactic Peptides on Cell Proliferation

To test whether the haptotactic peptides modulate cell proliferation, cells were incubated with a range of 1–50 uM concentrations of the peptides of interest for 3–4 days then the number of viable cells was determined with the MTS colorimetric assay. None of the peptides of SEQ ID NOs.: 1–10 affected the rate of proliferation of HF, BAEC or SMC relative to untreated controls.

Example 5

Uptake of FITC-Cβ and FITC-preCγ by Cells by Fluorescence Microscopy

Figure 3A:
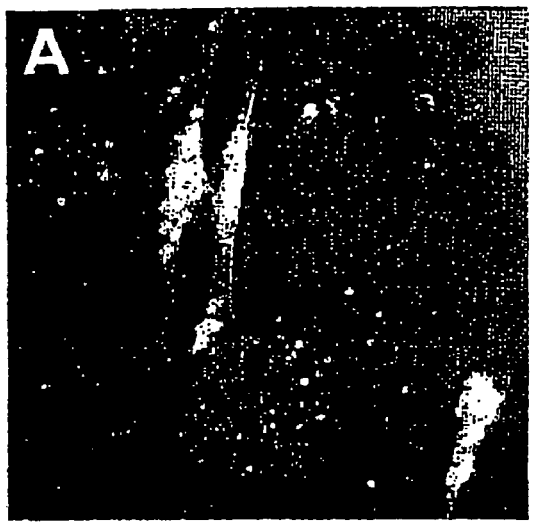
FIG. 3 Shows binding and internalization of dissolved 100 μg/ml A: Cβ$^{FITC}$, B: preCγ$^{FITC}$ (SEQ ID NO:1) and C: Cmfap (SEQ ID NO:5) by HF as viewed by fluorescent microscopy after 1 hr incubation. Cells initially accumulated tagged peptides at the cell membrane and eventually became distributed within the cytoplasm, to the perinuclear area and into granular bodies with little penetration into the nucleus.
Figure 3B:
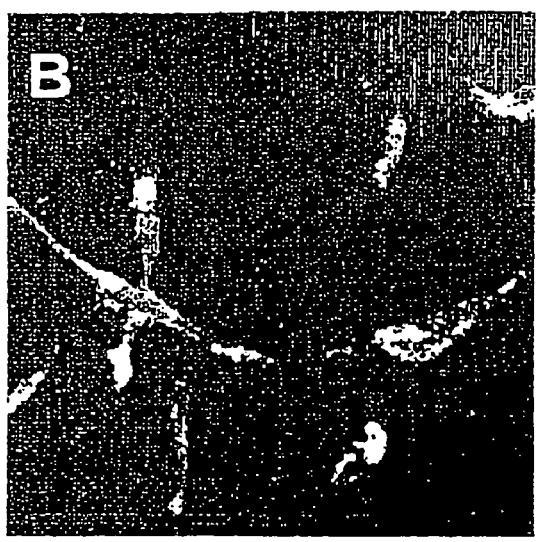
Figure 3C:
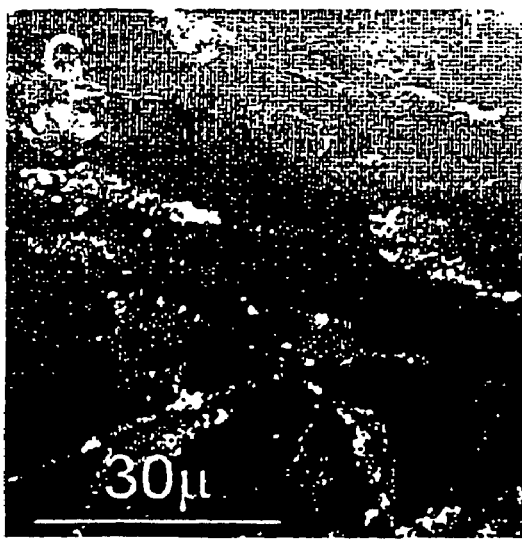

Exposure of cultured human fibroblast cells to a solution of 10 μM FITC peptide FITC-Cβ or preCγ (sequence ID #1) resulted in uptake into the cell cytoplasm, as shown by fluorescence microscopy (FIG. 3). After a longer exposure of more than 1 hour or with fixed cells, accumulation of the FITC-peptide in the cytoplasm and around the nucleus was clearly observed (data not shown). In most cases, the fluorescence became concentrated in discrete cytoplasmic vesicles.

These haptotactic peptides could be used to increase the cellularization of implants or to induce a better cellular contact with the implant. For example a peptide coated sponge implanted into bone tissue could induce osteogenic cells to migrate into and attach to the sponge and create improved new bone matrix at the site of the implant.

In another use, an electronic signaling or monitoring device coated with haptotactic peptides would exhibit improved binding to the cells within the implant area and be better incorporated into the tissue, thereby allowing its electronic functionality to be more efficient.

Polynucleotide sequences that encode for the amino acid sequences of the haptotactic peptides can be used to generate the peptides in genetically modified cells as is well known in the art. The DNA and RNA sequences can also be used for medical or diagnostic purposes. For example, one could monitor the mRNA sequences which encode for the haptotactic peptides to determine if those sequences are being biosynthesized by the cells or tissue being examined or if their synthesis is increased or decreased as a result of a therapeutic treatment or drug dosage.

Example 6

Binding of FITC-tagged Peptides to SB-Fib, SB-peptide or Liposomes

FITC-tagged peptides (10 μg/ml) were mixed with either SB-Fib, SB-Cb, incubated for 1 hour at ambient temperature, and visualized by confocal fluorescent microscopy. Similarly, 100 uL fibrin clot (2.4 mg/mL) was formed from fibrinogen and thrombin. After clot formation, 100 uL FITC-tagged peptides (10 μg/ml) were layered onto the clot, incubated for 1 hour at ambient temperature. The clot was washed with Tris buffer and visualized by confocal fluorescent microscopy. Fluorecsent micrographs reveal that the haptotactic fibrino-peptides bind to fibrinogen and to itself (i.e. SB-peptide). The interactions of haptotactic peptides with liposomes indicate that these peptides can bind to hydrophobic cell membranes and possibly to hydrophobic regions of large molecules.

Without wishing to be limited by a single mechanism, functional cell attachment features of fibrinogen chains and homologues of fibrinogen chain, as in Tables 2 and 3 are critical to the normal development and wound healing of all species. Peptide analogues of those in Tables 2 and 3 could be synthesized with non-natural synthetic amino acids or with D-amino acids, which would also provide a means of modulating the rate of peptide degradation within the cell and thereby prolong their biological lifetime, or create more selectivity to different cell types.

EXAMPLE 7

Coating of Matrices with Haptotactic Peptides Increases Cell Attachment in-vivo as Well as in-vitro 1. Cell culture model: A polymeric sponge containing free carboxy groups was covalently coated with haptotactic peptide according to known methods (38) as follows: Cβ peptide was coupled to the matrix by employing a water soluble carbodiimide reagent 1-Ethyl-3(3-dimethylaminopropyl) carbodiimide hydrochloride (EDC) (MW 191.7, Pierce Co) as follows: Matrix (100 mg) suspended in 2 ml conjugation buffer (0.1 M MES (2-[N-morpholinoethane sulfonic acid), pH 4.5–5). FITC-Cβ peptide (100 μl, 2 mg/ml) was added and the mixture stirred on an orbital shaker. EDC (2 mg) was added and the entire mixture was shaken at ambient temperature for 2 hours The reaction was stopped by adding 100 μl Tris/saline buffer and the matrix isolated. On the basis of the residual OD 280 of the supernatant, more than 70% of the FITC-peptide became coupled to the matrix to form peptide-matrix sponge.

A control polymeric sponge and Cβ-matrix sponge was incubated with trypsinized fibroblasts for over 10 days. Samples of sponge were removed at specified intervals (days 3 and 21), and were fixed and stained with propidium iodide to visualize cell nuclei. Confocal fluorescence micrographs show that relative to the untreated control sponge, the Cβ-treated sponge showed higher cellularization, namely an increase of cell content by more than 50% within 3 days, and the difference increased over a 21 day incubation period, where more than doubling of the the cell number was recorded. Similar results were obtained with other haptotactic peptides relative to untreated controls.

2. Animal model: Implant control sponge or Cβ-coated sponge under the skin of the back of rats and close the wounds. After 4.5 and 8 weeks, the animals were sacrificed and the implant areas examined histologically. In sets of control sponges, one could observe cells accumulating on the edges of the sponge and penetrating into the sponge inter-fibrous spaces. The cells form extracellular matrix with collagen deposition and granulation tissue, including the presence of giant cells and granulocytes and some inflammatory driven leukocytes. After 4.5 weeks, the sponges coated with Cβ peptide showed significantly-increased cellularity consisting of both fibroblasts and leukocytes and formation of more granulation tissue, relative to the control.

Example 8

Polynucleotide Sequences Encoding Haptotactic Peptides

Polynucleotide sequences that encode for the amino acid sequences of the haptotactic peptides can be used to generate the peptides in genetically modified cells as is well known in the art. The DNA and RNA sequences can also be used for medical or diagnostic purposes.

Without wishing to be limited, two examples of DNA sequences that encode for the amino acid sequences of the haptotactic peptides are as follows:

Cβ

DNA
. . . aagggtcatggtactcaatgaggaa-
gatgagtatgaagatcaggcccttcttcccaca
gcaa tag . . . (SEQ ID NO:16)

K G S W Y S M R K M S M K I R P F F P Q Q (SEQ ID NO:14)

Pre Cγ

DNA
. . . aaaacccggtggtattccatgaa-
gaaaaccactatgaagataatcccattcaacagact
caca . . . (SEQ ID NO:17)

K T R W Y S M K K T T M K I I P F N R L T (SEQ ID NO:1)

The amino acids of the haptotactic peptides can be encoded by other variant DNA sequences. The DNA and RNA sequences that code for the amino acids of the haptotactic peptides can be used for medical as well as diagnostic purposes.

While the invention has been described with respect to a limited number of embodiments, it will be appreciated that many variations, modifications and other applications of the invention may be made. The scope of the invention is not intended to be defined by the particular exemplifications used for illustrative purposes herein, but rather by the claims which follow.

REFERENCES

1. Mosesson M. and Doolittle R. (Eds). The Molecular Biology of Fibrinogen and Fibrin. Ann. N.Y. Acad. Sci. Volume 408: (1983).
2. Henschen A., Lottspeich F., Kehl M., Southan C. Covalent structure of fibrinogen. Ann. N.Y. Acad. Sci. 408: 28–43 (1983).
3. Spraggon G., Everse S. J., Doolittle R. F. Crystal structure of fragment D from human fibrinogen and its crosslinked counterpart from fibrin. Nature 389: 455–462 (1997).
4. Murakawa, M., Okamura, T., Kamura, T., Shibuya, T., Harada, M., Niho, Y. Diversity of primary structures of the carboxy-terminal regions of mammalian fibrinogen Aa-chains. Thrombosis & Haemostasis, 69:351–360, (1993).
5. Mosesson. M. Fibrinogen heterogeneity. Ann. N.Y. Acad. Sci. 408: 28–43 (1983).
6. Veklich Y I, Gorkun O V, Medved L V, Niewenjuizen W and Weisel J W. Carboxyl-terminal portions of the α chains of fibrinogen and fibrin. J. Biol. Chem. 268: 13577–13585 (1993).
7. Fu, Y. and Grieninger, G. Fib420: A normal human variant of fibrinogen with two extended α chains. Proc. Natl. Acad. Sci. USA, 91: 2625–2628, (1994).
8. Fu, Y, Weissbach, L., Plant, P. W., Oddoux, C., Cao, Y., Liang, T. J., Roy, S. N., Redman, C. M. and Grieninger, G. Carboxy-terminal-extended variant of the human fibrinogen α subunit: A novel exon containing marked homology to β and γ subunits. Biochem., 31:11968–11972 (1992).
9. Grieninger G., Lu X., Cao Y., Fu Y., Kudryk B. J., Galanakis D. K., Hertzberg K. M. Fib 420, a novel fibrinogen subclass: Newborn levels are higher than adult. Blood 90: 2609–2614 (1997).
19. Spraggon G, Applegate D, Everse S J, Zhang J Z, Veerapandian L, Redman C, Doolittle R F, Grieninger G. Crystal structure of a recombinant αE C domain from human fibrinogen 420. Proc. Natl. Acad. Sci USA 95: 9099–9104 (1998).
11. Gorodetsky, R., Vexler A., Shamir M., An J., Levdansky L., and Marx G. (1999). Fibrin microbeads (FMB) as biodegradable carriers for culturing cells and for accelerating wound healing. J. Invest. Dermatol. 112, 866–872 (1999).
12. Gorodetsky R., Vexler A., An J., Mou X, Marx G. Haptotactic and growth stimulatory effects of fibrin(ogen) and thrombin on cultured fibroblasts. J. Lab. Clin. Med. 131: 269–280 (1998).
13. Farrell D H & Thiagarajan P. Binding of recombinant fibrinogen mutants to platelets. J. Biol. Chem. 269: 226–231 (1994).
14. Thiagarajan P., Rippon A. J., Farrell D. H. Alternative adhesion sites in human fibrinogen for vascuilar endothelial cells. Biochemistry 35: 4169–4175 (1996).
15. Hantgan R R, Endenburg S, Cavero I, Marguerie G, Uzan A, Sixma J J and de Groot P G. Inhibition of platelet adhesion to fibrin(ogen) in flowing whole blood by RGD and fibrinogen γ chain carboxy terminal peptides. Thrombos. Haemostas. 68: 694–700 (1992).
16. Bednar B, Cunningham M E, McQueney P A, Egbertson M S, Askew B C, Bednar R A, Hartman G D, Gould R J. Flow cytometric measurement of kinetic and equilibrium binding parameters of arginine-glycine-aspartic acid ligands in binding to glycoprotein IIb/IIIa on platelets. Cytometry 28:1 58–65 (1997)
17. Varadi A. And Scheraga H. Localization of segments essential for polymerization and for calcium binding in the γ-chain 357–411 of human fibrinogen. Biochem. 25: 519–528 (1986).
18. Suehiro K; Mizuguchi J; Nishiyama K; Iwanaga S Farrell D H; Ohtaki S J Fibrinogen binds to integrin alpha(5)beta(1) via the carboxyl-terminal RGD site of the alpha-chain Biochem (Tokyo) 128(4):705–10 (2000)
19. Savage B., Bottini E. & Ruggeri Z M., Interaction of integrin alpha IIb beta with multiple fibrinogen domains during platelet adhesion, J. Biol. Chem. 270: 28812–7 (1995).
20. Thompson, W. D., Smith, E. B., Stirk, C. M., Marshall, F. I., Stout, A. J. and Kocchar, A., Angiogenic activity of fibrin degradation products is located in fibrin fragment E, J. Pathol., 168: 47–53 (1992).
21. Savage B., Bottini E. & Ruggeri Z M., Interaction of integrin alpha IIb beta IIIa with multiple fibrinogen domains during platelet adhesion. J. Biol. Chem. 270: 28812–7 (1995).
22. Gray, A. J., Bishop, J. E., Reeves, J. T. and Laurent, G. J.; Aα and Bβ Chains of fibrinogen stimulate proliferation of human fibroblasts. J. Cell Sci., 104: 409–413, (1993)).
23. Saldeen T: Vasoactive peptides derived from degradation of fibrinogen and fibrin. Proc. NY Acad Sci USA, 408: 424–431 (1983)).
24. Suri C., Jones P. F., Patan S., Bartunkova S., Maisonpierre P. C., Daavais S., Sato T. N., Yancopulos G. D. Requisite role of angiopoietin 1, a ligand for the TIE2 receptor during embryonic angiogenisis. Cell 87: 1171–80 (1996).
25. Maisonpierre P. C. et al. Angiopoietin-2, a natural antagonist for Tie2 that disrupts in vivo angiogenisis. Science 277: 55–60 (1996).
26. Partanen J., Armstrong E., Makela T., Korhonen J., Sandberg M., Renkonen R., Knuutila S., Huebner K., Alitalo K. A novel endothelial cell surface receptor tyrosine kinase with extracellular epidermal growth factor homology domains. Molec. Cell. Biol. 12 1698–1707 (1992).
27. Sato T. Qin Y., Kozak C. A., Audus K. L. Tie-1 and Tie-2 define another class of putative receptor tyrosine kinase genes expressed in early embryonic vascular system. Proc. Natl. Acad. Sci. USA 90: 9355–58 (1993).
31. Sato T. N., Tozawa Y. Deutsch U., Wolburg-Buchholz K., Fujiwara Y., Gendron-Maguire M., Gridley T., Wolburg H., Risau W., Qin Y. Distinct roles of the receptor tyrosine kinases Tie-1 and Tie-2 in blood vessel formation. Nature 376: 70–74 (1995).
28. Mustonen T., Alitalo K. Endothelial receptor tyrosine kinases involved in angiogenisis. J. Cell Biol. 129: 895–898 (1995).
29. Hashiyama M., Iwama A., Oshira K., Kurozumi K., Yasunaga K., Shimizu Y., Masuho Y., Matsuda I., Yamaguchi N., Suda T. Predominant expression of receptor tyrosine kinase, TIE, in hematopoietic stem cells and B cells. Blood 87: 93–101 (1996).
30. Zhao Z, Lee C, Jiralerspong S, Juyal R C, Lu F, Baldini A, Greenberg F, Caskey C T, Patel P I. The gene for a human microfibril-associated glycoprotein is commonly deleted in Smith-Magenis syndrome patients. Hum Mol Genet Apr 4:4 589–97 (1995).
31. Xia S., Ozsvath K., Hirose H., Tilson M. D. Partial amino acid sequence of a novel 40 kDa human aortic protein, with vitronectin-like fibrinogen-like and calcium binding domains: Aortic aneurysm-associated protein-40 (AAAP40) [human MAGP-3, proposed]. Biochem. Biophys. Res. Comm. 219: 36–39 (1996).
32. Kobayashi R., Mizutani A., Hikada H. Isolation and characterization of a 36-kDa microfibril-associated gly coprotein by the newly synthesized isoquinoline sulfonamide affinity chromatography. Biochem. Biophys. Res. Comm. 198: 1262–1266 (1994).
33. Zhao Z, Lee C, Jiralerspong S, Juyal R C, Lu F, Baldini A, Greenberg F, Caskey C T, Patel P I. The gene for a human microfibril-associated glycoprotein is commonly deleted in Smith-Magenis syndrome patients. Hum Mol Genet 4 589–97 (1995)
34. Brown-Augsburger P, Broekelmann T, Rosenbloom J, Mecham R P. Functional domains on elastin and microfibril-associated glycoprotein involved in elastic fibre assembly [published erratum appears in Biochem J 1997, 863: Biochem J Aug 15 318 (Pt 1): 149–55. (1996) (check ref):
35. Erickson H. P. Tenascin-C, tenascin-R and tenascin-X: a family of talented proteins in search of functions. Curr. Op. Cell Biol. 5: 869–76 (1993).
36. Zhi-Cheng Xiao, David S. Ragsdale, Jyoti Dhar Malhotra, Laura N. Mattei, Peter E. Braun, Melitta Schachner, and Lori L. Isom Tenascin-R Is a Functional Modulator of Sodium Channel Subunits. J Biol Chem, 274: 26511–26517, 1999.
37. Jayashree Srinivasan, Melitta Schachner, and William A. Catterall Interaction of voltage-gated sodium channels with the extracellular matrix molecules tenascin-C and tenascin-R. PNAS. 95: 15753–15757, 1998.
38. Timkovich, R. (1977). Detection of the stable addition of carbodiimide to proteins. Anal. Biochem. 79,135–143.

The invention claimed is:

1. An isolated haptotactic peptide of 20 amino acids consisting of the amino acid sequence as set forth in SEQ ID NO:1, characterized in that the haptotactic peptide induces cell attachment to a surface to which the haptotactic peptide is covalently bound, inasmuch as the number of cells attached to the surface is at least 50% greater than the number of cells attached to the surface in the absence of the peptide.

2. An isolated haptotactic peptide consisting of an active fragment of the 20 amino acid sequence set forth in SEQ ID NO:1, wherein the active fragment comprises an amino acid sequence selected from the group consisting of sequences set forth in SEQ ID NO:11 or SEQ ID NO:12 and is characterized in that the haptotactic peptide induces cell attachment to a surface to which the haptotactic peptide is covalently bound, inasmuch as the number of cells attached to the surface is at least 50% greater than the number of cells attached to the surface in the absence of the peptide.

3. A composition, comprising the isolated haptotactic peptide of claim 1, and a carrier.

4. The composition of claim 3, wherein said haptotactic peptide is for covalent attachment to the surface of a medical device.

5. The composition of claim 4, wherein said medical device is a medical implant.

6. The composition of claim 3, wherein said haptotactic peptide is covalently attached to a bead.

7. The composition of claim 3, wherein said haptotactic peptide is covalently attached to a matrix.

8. The composition of claim 3, further comprising at least one isolated haptotactic peptide having a sequence other than the sequence set forth in SEQ ID NO:1.

9. The composition of claim 3, wherein the haptotactic peptide is derivatized with a fluorescent tag.

10. The composition of claim 3, wherein the haptotactic peptide is derivatized with a radioactive tag.

11. A composition comprising the isolated haptotactic peptide of claim 2 and a carrier.

12. The composition of claim 11, further comprising at least a drug or biological agent.

13. The composition of claim 12, wherein said haptotactic peptide is covalently attached to a drug.

14. The composition of claim 11, further comprising a plurality of cells selected from the group consisting of mesenchymal cells, parenchymal cells, fibroblasts, endothelial cells, chondrocytes, kidney cells, liver cells, pancreatic cells, thyroid cells, glial cells, astrocytes, smooth muscle cells and myofibroblasts, to which the peptide is attached.

15. The composition of claim 11, further comprising a plurality of cells selected from the group consisting of immortalized cells, transformed cells, mammary carcinoma cells, 3T3 fibroblasts, malignant melanoma cells and ovarian carcinoma cells, to which the peptide is attached.

16. The composition of claim 15, wherein said cells are selected from the group consisting of pluripotent cells capable of differentiating into fibroblasts, myofibroblasts, smooth muscle cells, endothelial cells, and combinations thereof.

17. The composition of claim 15, wherein said cells are selected from the group consisting of neural cells, glial cells, astrocytes, and combinations thereof.

18. The composition of claim 15, wherein said cells are selected from the group consisting of cells derived from bone marrow, blood or buffy-coat capable of differentiating into osteoblasts, chondrocytes, and combinations thereof.

19. The composition of claim 15, wherein said cells are selected from the group consisting of immortalized cells and hybridomas.

20. A device comprising the isolated haptotactic peptide of claim 1, wherein said haptotatric peptide is covalently attached to the surface of the device.

* * * * *